US00PP21192P2

(12) United States Plant Patent

Hardison et al.

(10) Patent No.: US PP21,192 P2

(45) Date of Patent: *Aug. 10, 2010

(54) HYBRID VARIETY OF TEXAS×KENTUCKY BLUEGRASS DESIGNATED 'HB 130'

(50) Latin Name: *Poa arachnifera Torr.×Poa pratensis L.*
Varietal Denomination: HB 130

(75) Inventors: John R. Hardison, Corvallis, OR (US); Jay B. Burr, Salem, OR (US); James R. Frelich, Salem, OR (US); George Marquez, Albany, OR (US)

(73) Assignee: OMS Investments, Inc., Los Angeles, CA (US)

( * ) Notice: Subject to any disclaimer, the term of this patent is extended or adjusted under 35 U.S.C. 154(b) by 885 days.

This patent is subject to a terminal disclaimer.

(21) Appl. No.: 11/483,919

(22) Filed: Jul. 10, 2006

(51) Int. Cl.
*A01H 5/00* (2006.01)

(52) U.S. Cl. ..... Plt./393

(58) Field of Classification Search ..... Plt./393
See application file for complete search history.

(56) References Cited

OTHER PUBLICATIONS

U.S. Appl. No. 60/545,026, filed Feb. 2004, Guo et al.*

PI 603946—*Poa arachnifera*—Reveille —Texas, United States (2 pages).

* cited by examiner

*Primary Examiner*—Annette H Para

(74) *Attorney, Agent, or Firm*—Hunton & Williams LLP

(57) ABSTRACT

A hybrid variety of Texas bluegrass×Kentucky bluegrass as described, characterized by rapid establishment; a light green, dense turf; a wide leaf blade; aggressive rhizome growth; a reduced level of cotton on the seed; and a medium to high seed yield potential.

2 Drawing Sheets

BACKGROUND OF THE INVENTION

Field of the Invention

The present invention relates to a new and distinct hybrid variety of *Poa arachnifera* Torr.×*Poa pratensis* L. that has been designated as 'HB 130' bluegrass.

Description of Related Art

A *Poa arachnifera*×*Poa pratensis* hybrid designated 'Reveille' has been disclosed in PVP Certificate No. 9800337. Another *Poa arachnifera* Torr.×*Poa pratensis* L. hybrid designated as 'HB 129' has been disclosed in pending U.S. patent application Ser. No. 11/197,945, filed Aug. 5, 2005, claiming the benefit of provisional application No. 60/599,539, filed Aug. 6, 2004. 'HB 129' is commercially available as 'Thermal Blue' and this commercial designation is used elsewhere herein. U.S. patent application Ser. No. 11/208,473, filed Aug. 19, 2005 described another *Poa arachnifera* Torr.×*Poa pratensis* L. hybrid designated as 'HB 329' as the progeny formed by crossing an interspecific hybrid bluegrass (Texas Bluegrass×Kentucky Bluegrass) designated 'HB 47' (a female plant 7-23 ×cv. 'Geronimo' male plant) as the female parent crossed with cv. 'Ascot' Kentucky bluegrass (*Poa pratensis* L.) as the pollen parent. 'HB 329' is commercially available as 'Dura Blue' and this commercial designation is used elsewhere herein.

SUMMARY OF THE VARIETY

'HB 130' bluegrass is the result of a plant selected from the progeny of Texas bluegrass (*Poa arachnifera* Torr.) female plant 6-8 (seed parent), with cv. 'Geronimo' Kentucky bluegrass (pollen parent)(*Poa pratensis* L.) cross for perfect flowers, apomixis and turfgrass performance characteristics in the $F_1$ generation.

Texas bluegrass female plant 6-8 is an unpatented, unreleased plant selected and maintained for its tiller density, turf quality and the lack of male reproductive organs. The cv. 'Geronimo' is an unpatented, released Kentucky bluegrass of European origin from Mommersteeg International, Vlijmen, the Netherlands.

As a result of this breeding, a distinct variety was produced and asexually propagated by rhizomes, tillers and disseminules. The highly apomictic seed of 'HB 130' bluegrass was produced first at Corvallis, Oreg. This seed was used to plant turf performance evaluation trials and later, seed production fields.

The seed of 'HB 130' has been found to be stable. Asexual production of 'HB 130' initially was performed at Corvallis, Oreg. by propagules (tillers and rhizomes) and by disseminules (modified caryopses produced by apomixis), and has consistently produced progeny plants indistinguishable from the first generation asexual reproductions of the instant plant. The apomixis level of 'HB130' is approximately 86%. The apomixis level was determined by examining Greenhouse grow-outs of 'HB 130' rating for apomictic origin from disseminules harvested from three growing seasons from field grown 'HB 130' plants in Gervais, Oreg.

The 'HB 130' grass described herein is a high-quality, aggressive bluegrass hybrid with a number of highly desirable characteristics, including aggressive establishment, excellent recoverability, heat tolerance better in tall fescue regions of the U.S., shade tolerance, a finer texture than tall fescue, resistance to brown patch and *Pythium*. 'HB 130' resists disease in humid regions better than traditional Kentucky bluegrasses, and is acclimated to colder northern climates as well as high heat areas.

'HB 130' thrives under traditional Kentucky bluegrass maintenance programs in the cool season zone. 'HB 130' has an upright leafy turf type, and a medium green color that can be maintained throughout the entire growing season. 'HB 130' demonstrates good fall color and good winter color under mild winter conditions.

Texas bluegrass is a vigorous sod-forming perennial native in the Southeastern and Southern Plains States. Plants grow up to 3 feet on strong soil, with numerous leaves 6 to 12 inches long and 0.025 inch wide. The grass grows throughout the winter producing abundant, nutritious pasture which is highly palatable. This is a valuable species where native, but seeding is difficult. The species is dioecious, with male and female plants. It produces only limited quantities of seed which is covered with woolly hairs that are difficult to remove. Consequently, establishment of stands for agricultural use is limited. Reveille variety Kentucky bluegrass exhibits problems similar to those encountered with Texas bluegrass; these problems are overcome employing the present 'HB 130' hybrid.

'HB 130' has reduced cotton (webbing) on the lemma relative to 'HB 129', 'Reveille', and parental Texas bluegrasses. 'HB 130' has a medium to high seed yield potential in the Kentucky bluegrass seed production region of the northwestern United States and has shown the potential for economic seed production.

In comparison with Texas bluegrasses, 'Reveille' hybrid bluegrass and 'Ascot' and Coventry varieties of Kentucky bluegrass, 'HB 130' has demonstrated relatively rapid germination and emergence in both fall and spring sowings. 'HB 130' has shown greatly reduced seed cotton as compared with 'Reveille'. It is believed that the presence of the cotton on the 'Reveille' seed results in poor seed recovery of the hybrid and causes 'Reveille' to be available predominantly as a vegetatively reproduced product from rhizome and tiller materials.

In comparison with a number of Kentucky bluegrass varieties 'HB 130' has an above-average seed size with a lower number of seeds per pound.

DETAILED DESCRIPTION OF THE VARIETY

Figure 1:
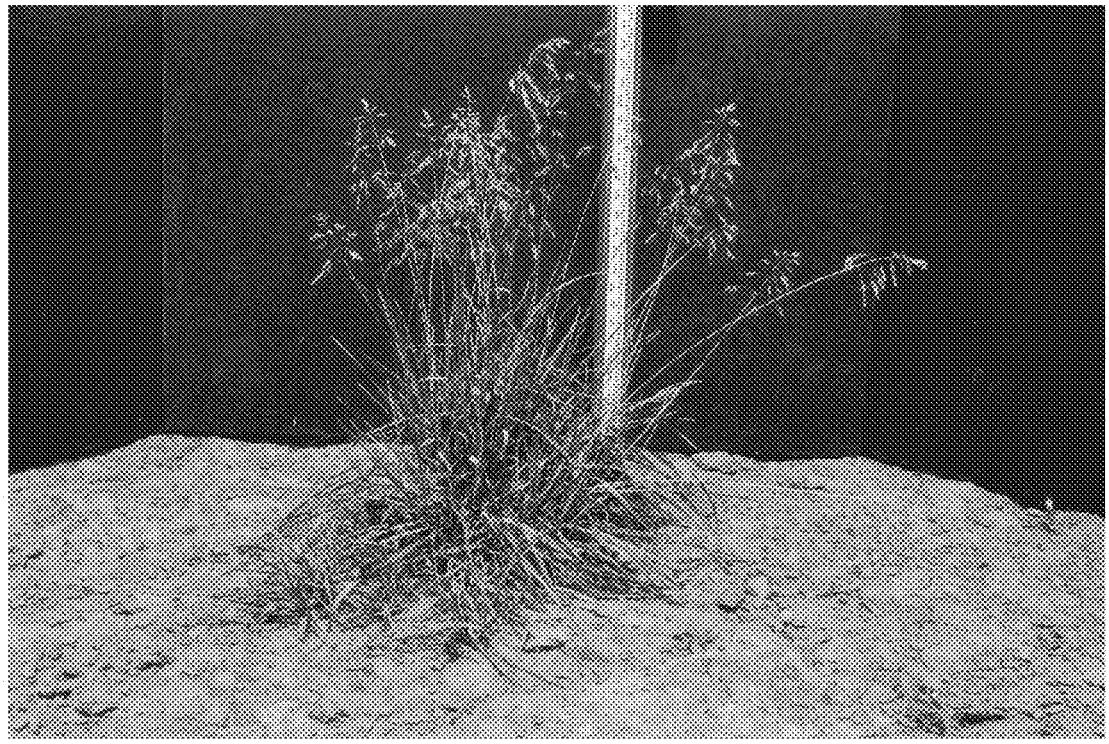
FIG. 1 is an 'HB 130' panicle.
Figure 2:
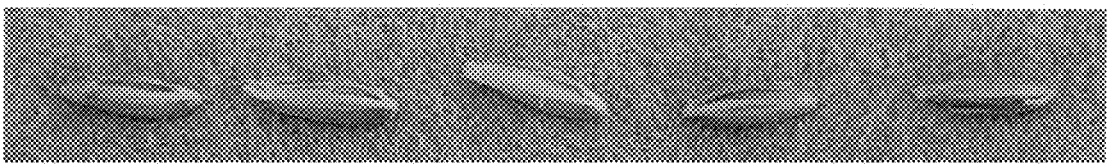
FIG. 2 is an 'HB 130' seed.
Figure 3:
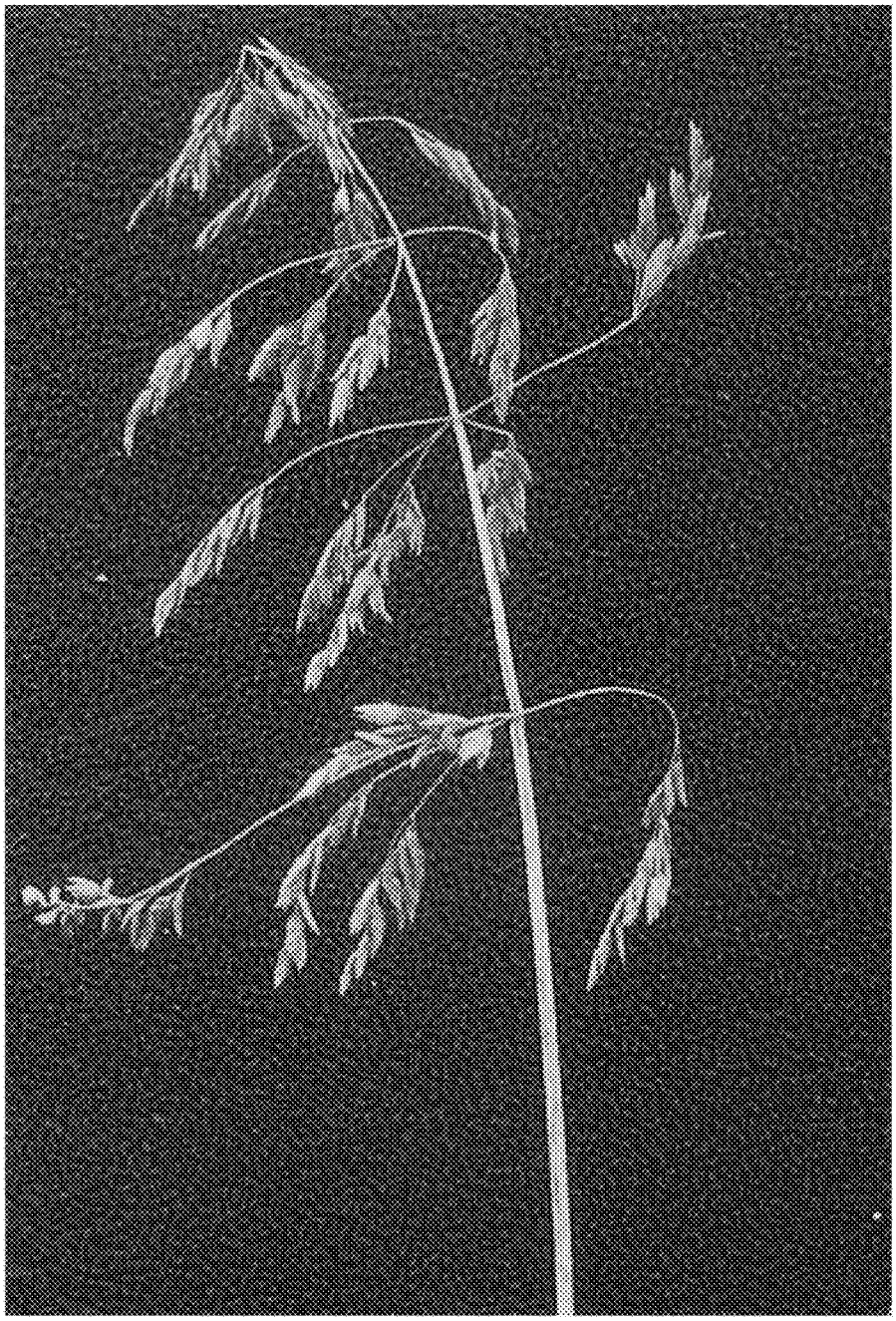
FIG. 3 is an 'HB 130' plant shortly after completing anthesis.

'HB 130' Texas bluegrass×Kentucky bluegrass (*Poa arachnifera* L.×*Poa pratensis* L.) hybrid is perennial with creeping rhizomes forming a dense turf. When plants overwinter in the field and grow undisturbed by clipping, culms are semi-erect averaging 63.0 cm. The vegetative leaf averages 9.0 cm in length. The flag leaf averages 6.5 cm in length. 3.55 mm in width, and has a sheath length of 15.4 cm. The flag leaf averages more hairs on the ligule than 'HB 329', 'Reveille', and Texas bluegrass varieties but fewer than 'HB 129', 'Ascot', or 'Geronimo' variety Kentucky bluegrasses.

'HB 130' is an aggressive and durable bluegrass, making it suitable for athletic fields. 'HB 130' spread the most of tested varieties. Only Thermal Blue and Geronimo varieties showed similar plant area spread, whereas all other cultivars spread much less in a growing season.

TABLE 1

Plant Spread Area. Comparison of plant spread reported in square centimeters at The Scotts Company facility, Gervais, Oregon

| Cultivar | Plant spread Area ($cm^2$) |
|---|---|
| 'HB 130' | 2375.85 |
| 'Thermal Blue' | 2279.07 |
| 'Geronimo' | 2177.94 |
| 'Buckingham' | 1330.18 |
| 'Reveille' | 1209.80 |
| 'Dura Blue' | 1096.47 |
| 'Kelly' | 982.25 |
| 'Ascot' | 949.65 |
| 'Midnight' | 912.37 |
| 'Tx 51-90' | 672.42 |
| 'Tx 39-88' | 384.52 |
| 'Tx 49-90' | 336.63 |
| 'HB96' | 295.28 |
| lsd (p = 0.05) | 653.17 |

TABLE 2

Tiller characteristics of 'HB 130' and various Kentucky and Texas bluegrass cultivars at The Scotts Company facility, Gervais, Oregon. Measurements in centimeters and nodes per tiller.

| Cultivar | Culm length | Nodes on tiller | Top internode length |
|---|---|---|---|
| 'HB 130' | 58.5 | 3.9 | 13.1 |
| 'Thermal Blue' | 59.2 | 4.7 | 13.5 |
| 'Dura Blue' | 52.6 | 4.2 | 17.8 |
| 'Geronimo' | 59.3 | 4.1 | 15.5 |
| 'Ascot' | 47.0 | 4.8 | 10.8 |
| 'Tx 39-88' | 70.0 | 3.8 | 9.5 |
| 'Tx 49-90' | 61.7 | 3.4 | 9.8 |
| lsd (0.05) | 7.63 | 0.86 | 3.15 |

TABLE 3

Tiller characteristics of 'HB 130' and various Kentucky and Texas bluegrass cultivars at The Scotts Company facility, Gervais, Oregon. Measurements in centimeters and nodes per tiller.

| Cultivar | Culm length | Nodes on tiller | Top internode length |
|---|---|---|---|
| 'HB 130' | 63.0 | 4.4 | 11.5 |
| 'Thermal Blue' | 64.8 | 4.5 | 11.3 |
| 'Dura Blue' | 52.3 | 3.2 | 17.0 |
| 'Geronimo' | 67.6 | 4.7 | 12.5 |
| 'Ascot' | 52.4 | 4.1 | 9.7 |
| 'Tx 39-88' | 59.6 | 2.2 | 9.9 |
| 'Tx 49-90' | 66.5 | 2.4 | 9.7 |
| lsd (p = 0.05) | 7.77 | 1.1 | 3.39 |

TABLE 4

Comparison of morphological traits of flowering tiller of plants allowed to over winter in the field and placed into a controlled greenhouse environment (60-75 F.) in late winter and allowed to grow undisturbed during a winter season at The Scotts Company facility, Gervais, Oregon.

| Cultivar | Culm Length (cm) | Peduncle Length (cm) | Peduncle Width (cm) | Flag Leaf Subtending Internode Length (cm) | Nodes on Culm (#) |
|---|---|---|---|---|---|
| 'HB 130' | 72.1 | 32.9 | 0.99 | 16.1 | 2.9 |
| 'Thermal Blue' | 63.6 | 28.1 | 0.80 | 17.8 | 3.7 |

TABLE 4-continued

Comparison of morphological traits of flowering tiller of plants allowed to over winter in the field and placed into a controlled greenhouse environment (60-75 F.) in late winter and allowed to grow undisturbed during a winter season at The Scotts Company facility, Gervais, Oregon.

| Cultivar | Culm Length (cm) | Peduncle Length (cm) | Peduncle Width (cm) | Flag Leaf Subtending Internode Length (cm) | Nodes on Culm (#) |
|---|---|---|---|---|---|
| 'Dura Blue' | 54.0 | 19.3 | 0.71 | 22.9 | 3.0 |
| 'Reveille' | 72.1 | 34.9 | 0.99 | 16.1 | 2.9 |
| 'Geronimo' | 69.8 | 31.3 | 0.87 | 19.3 | 3.5 |
| 'Ascot' | 62.2 | 28.9 | 0.87 | 17.8 | 3.2 |
| 'Kelly' | 65.0 | 31.8 | 0.96 | 18.2 | 3.5 |
| 'Tx 51-90' | 64.7 | 35.7 | 1.02 | 14.5 | 2.3 |
| 'Tx 39-88' | 68.3 | 43.8 | 1.20 | 14.9 | 2.3 |
| 'TX 49-90' | 68.3 | 35.4 | 1.05 | 19.1 | 2.5 |
| lsd (p = 0.05) | 10.20 | 7.13 | 0.160 | 4.58 | 0.63 |

When grown in nurseries over one or two seasons, 'HB 130' has shown uniformly open panicles, with drooping panicle branches. The panicle averaged 10.7 cm in length and 10.8 cm in width, exceeding the panicle dimensions of 'HB 129' and 'HB 329' both in nurseries and when grown in controlled greenhouse environments, as set forth below. 'HB 130' panicles showed little to no variation from year to year in panicle shape and branch attitude, while variation was observed in the comparator cultivars.

TABLE 5

Comparison panicle type of 'HR 130' with various Kentucky and Texas bluegrass cultivars planted at The Scotts Company facility, Gervais, Oregon. (Rating Scale: 1 = open panicle, 2 = intermediate panicle, 3 = compact panicle).

| Cultivar | Year 1 |
|---|---|
| 'HB-130' | 1.0 |
| 'Thermal Blue' | 1.0 |
| 'Dura Blue' | 1.0 |
| 'Abbey' | 1.0 |
| 'Ascot' | 1.0 |
| 'Geronimo' | 1.0 |
| 'TX 19-88' | 1.0 |
| 'TX 46-90' | 1.7 |
| 'TX 4-88' | 2.0 |
| lsd (p = 0.05) | 0.36 |

TABLE 6

Panicle branch attitude for 'HB 130' and various Kentucky and Texas bluegrass cultivars planted at The Scotts Company facility, Gervais, Oregon for 1 and 2 years. (Rating Scale: 1 = Drooping, 2 = Horizontal, 3 = Ascending)

| Cultivar | Year 1 | Year 2 |
|---|---|---|
| 'HB-130' | 1.0 | 1.0 |
| 'Thermal Blue' | 1.1 | 1.0 |
| 'Dura Blue' | 1.1 | 1.5 |
| 'Abbey' | 1.1 | 1.0 |
| 'Ascot' | 1.5 | 1.0 |
| 'Geronimo' | 1.2 | 1.3 |
| 'TX 19-88' | 3.0 | 3.0 |
| 'TX 46-90' | 2.5 | 2.9 |
| 'TX 4-88' | 1.5 | 2.8 |
| lsd (p = 0.05) | 0.35 | 0.54 |

TABLE 7

Panicle shape variation for 'HB 130' and various Kentucky and Texas bluegrass cultivars planted at Gervais, Oregon, in percent.

| Cultivar | Open | Intermediate | Compact |
|---|---|---|---|
| 'HB 130' | 100.0 | 0 | 0 |
| 'Thermal Blue' | 96.8 | 3.2 | 0 |
| 'Dura Blue' | 92.6 | 7.4 | 0 |
| 'Geronimo' | 100.0 | 0 | 0 |
| 'Ascot' | 98.3 | 1.7 | 0 |
| 'Tx 39-88' | 0 | 15.4 | 84.7 |
| 'Tx 49-90' | 0 | 25.7 | 74.3 |
| lsd (p = 0.05) | 12.8 | 15.4 | 10.2 |

TABLE 8

Panicle characteristics of plants allowed to over winter (vernalize) in the field and placed into a controlled greenhouse environment (60-75 F.) in late winter and allowed to grow undisturbed during a winter season at The Scotts Company facility, Gervais, Oregon

| Cultivar | Panicle Branches in 1st whorl (count) | Panicle Branches in 3rd whorl (count) | Panicle Length (cm) | Panicle Width (cm) |
|---|---|---|---|---|
| 'HB 130' | 3.7 | 2.9 | 9.2 | 7.6 |
| 'Thermal Blue' | 4.0 | 2.7 | 7.3 | 6.7 |
| 'Dura Blue' | 3.2 | 2.5 | 8.0 | 6.8 |
| 'Reveille' | 5.0 | 4.2 | 9.7 | 5.9 |
| 'Geronimo' | 3.5 | 2.8 | 8.6 | 7.3 |
| 'Ascot' | 2.3 | 2.1 | 8.2 | 7.2 |
| 'Tx 51-90' | 4.5 | 3.6 | 9.2 | 4.0 |
| 'Tx 39-88' | 3.8 | 3.3 | 9.2 | 4.1 |
| lsd (p = 0.05) | 0.72 | 0.39 | 0.76 | 0.93 |

TABLE 9

Branches in first and third whorl for 'HB 130' and various Kentucky and Texas bluegrass cultivars in nurseries planted at The Scotts Company facility, Gervais, Oregon.

| Cultivar | Branches in 1st whorl (count) 2004 | Branches in 1st whorl (count) 2005 | Branches in 3rd whorl (count) 2004 | Branches in 3rd whorl (count) 2005 |
|---|---|---|---|---|
| 'HB 130' | 3.9 | 4.3 | 3.2 | 3.3 |
| 'Thermal Blue' | 4.0 | 4.0 | 3.3 | 3.2 |
| 'Dura Blue' | 4.4 | 3.8 | 3.8 | 3.1 |
| 'Geronimo' | 4.0 | 4.4 | 3.5 | 3.1 |
| 'Ascot' | 2.8 | 3.8 | 2.4 | 2.2 |
| 'Tx 19-88' | 5.3 | — | — | — |
| 'Tx 49-90' | 4.9 | — | 5.0 | — |
| 'Tx 39-88' | — | 2.5 | — | 2.8 |
| 'Tx 46-90' | — | 3.8 | — | 3.2 |
| lsd (0.05) | 0.82 | 0.93 | 0.78 | 1.08 |

TABLE 10

Panicle dimensions for 'HB 130' and various Kentucky and Texas bluegrass cultivars in nurseries planted at The Scotts Company facility, Gervais, Oregon

| Cultivar | Length (cm) | Length (cm) | Width (cm) | Width (cm) |
|---|---|---|---|---|
| 'HB 130' | 9.3 | 10.7 | 8.5 | 10.8 |
| 'Thermal Blue' | 9.1 | 10.5 | 8.4 | 10.3 |
| 'Dura Blue' | 8.6 | 9.7 | 6.9 | 8.5 |
| 'Geronimo' | 8.9 | 11.1 | 8.1 | 11.4 |
| 'Ascot' | 7.6 | 9.3 | 7.0 | 8.9 |

TABLE 10-continued

Panicle dimensions for 'HB 130' and various Kentucky and Texas bluegrass cultivars in nurseries planted at The Scotts Company facility, Gervais, Oregon

| Cultivar | Length (cm) | Length (cm) | Width (cm) | Width (cm) |
|---|---|---|---|---|
| 'Kelly' | — | 9.8 | — | 9.4 |
| 'Tx 19-88' | 12.9 | — | 9.8 | — |
| 'Tx 49-90' | 13.5 | — | 9.5 | — |
| 'Tx 39-88' | — | 11.5 | — | 9.1 |
| 'Tx 46-90' | — | 9.6 | — | 7.4 |
| lsd (p = 0.05) | 2.65 | 2.51 | 1.24 | 1.91 |

TABLE 11

'HB 130' Comparison of morphological traits of plant inflorescence - spikelets, florets, glumes - from panicles harvested from a field nursery and plant height at The Scotts Company facility at Gervais, Oregon. (Measurement in millimeters).

| Variety | Spikelet Length 1st Whorl | Spikelet Length 3rd Whorl | Spikelet Width 1st Whorl | Spikelet Width 3rd Whorl |
|---|---|---|---|---|
| 'HB 130' | 6.4 | 6.7 | 4.2 | 3.6 |
| 'Thermal Blue' | 7.6 | 7.1 | 4.5 | 4.0 |
| 'Dura Blue' | 6.2 | 6.5 | 4.3 | 3.8 |
| 'Reveille' | 6.1 | 6.4 | 4.0 | 4.2 |
| 'Geronimo' | 5.5 | 6.3 | 4.2 | 4.0 |
| 'Ascot' | 5.6 | 5.8 | 4.4 | 4.3 |
| 'Midnight' | 5.7 | 6.4 | 2.7 | 3.2 |
| 'Buckingham' | 6.9 | 6.9 | 4.6 | 4.7 |
| 'TX 51-90' | 7.6 | 7.5 | 7.3 | 7.1 |
| 'TX 39-88' | 8.6 | 8.5 | 5.9 | 5.7 |
| 'TX 49-90' | 9.7 | 9.7 | 8.2 | 8.0 |
| 'Kelly' | 6.3 | 6.1 | 4.4 | 4.3 |
| lsd (p = 0.05) | 1.679 | 1.738 | 1.875 | 1.621 |

| Variety | Florets Spikelet 1st Whorl | Florets Spikelet 3rd Whorl | Lower Glume Length 1st Whorl | Lower Glume Length 3rd Whorl |
|---|---|---|---|---|
| 'HB 130' | 6.3 | 6.4 | 3.0 | 3.0 |
| 'Thermal Blue' | 8.6 | 7.0 | 3.1 | 3.2 |
| 'Dura Blue' | 4.6 | 5.0 | 3.7 | 3.6 |
| 'Reveille' | 4.0 | 4.9 | 2.9 | 3.3 |
| 'Geronimo' | 5.2 | 6.0 | 2.7 | 3.0 |
| 'Ascot' | 3.8 | 4.3 | 2.9 | 2.9 |
| 'Midnight' | 4.3 | 5.8 | 2.7 | 2.6 |
| 'Buckingham' | 6.7 | 7.1 | 3.1 | 3.0 |
| 'TX 51-90' | 8.8 | 8.5 | 3.6 | 3.3 |
| 'TX 39-88' | 8.0 | 7.9 | 3.6 | 3.6 |
| 'TX 49-90' | 8.7 | 8.6 | 5.4 | 5.0 |
| 'Kelly' | 4.3 | 4.9 | 2.8 | 2.9 |
| lsd (p = 0.05) | 1.69 | 1.81 | 0.853 | 0.682 |

| | Upper Glume Length 1st Whorl | Upper Glume Length 3rd Whorl | Plant Height |
|---|---|---|---|
| 'HB 130' | 3.0 | 3.2 | 54.6 |
| 'Thermal Blue' | 3.5 | 3.3 | 58.3 |
| 'Dura Blue' | 3.6 | 3.7 | 38.8 |
| 'Reveille' | 3.3 | 3.5 | 51.6 |
| 'Geronimo' | 2.9 | 3.1 | 56.9 |
| 'Ascot' | 3.1 | 3.1 | 38.2 |
| 'Midnight' | 3.1 | 3.2 | 29.7 |
| 'Buckingham' | 3.4 | 3.4 | 48.2 |
| 'TX 51-90' | 4.2 | 4.2 | 48.1 |
| 'TX 39-88' | 4.0 | 4.2 | 60.4 |
| 'TX 49-90' | 6.0 | 5.4 | 56.2 |
| 'Kelly' | 3.0 | 3.0 | 38.0 |
| lsd (p = 0.05) | 0.951 | 0.803 | 8.807 |

As demonstrated by the tabulated results in Table 11, the spikelet length in both the 1st and 3rd whorl of the panicle branch of 'HB 130' is less than in Texas bluegrass but greater than Reveille, Geronimo, Ascot and Midnight.

For the vegetative leaf, the number of hairs is average for the leaf sheath margin, above average for the dorsal side of the leaf blade, above average for the upper margin of the ligule, and below average for the collar margin compared to other varieties. 'HB 130' differs from the Kentucky bluegrass varieties in regard to such morphological characteristics as seed length and width, culm length, and hairs on the collar margins of the vegetative leaf, on the upper surface of the vegetative leaf, on the ligule of the flag leaf, and aggressive growth. As shown in Table 12, 'HB 130' has a shorter flag leaf ligule, more hairs on the flag leaf ligule and has a thinner flag leaf than Reveille hybrid Kentucky bluegrass and Texas bluegrass.

TABLE 12

Ligule thickness, ligule hairs and flag leaf thickness of 'HB 130' and other hybrid bluegrasses, parental varieties and germplasms planted at The Scotts Company facility, Gervais, Oregon. (Measurements in millimeters).

| Cultivar | Ligule Length | Ligule Hairs | Thickness |
|---|---|---|---|
| 'HB 130' | 1.7 | 4.5 | 0.015 |
| 'Thermal Blue' | 1.3 | 5.8 | 0.015 |
| 'Dura Blue' | 2.3 | 3.2 | 0.018 |
| 'Reveille' | 2.3 | 0.9 | 0.021 |
| 'Ascot' | 2.0 | 5.6 | 0.017 |
| 'Geronimo' | 1.7 | 7.1 | 0.016 |
| 'Tx 51-90' | 1.7 | 0.1 | 0.026 |
| 'Tx 39-88' | 2.7 | 0.1 | 0.020 |
| 'Tx 49-90' | 2.0 | 0.5 | 0.023 |
| lsd (0.05) | 0.66 | 1.9 | 0.0033 |

As demonstrated by the tabulated results in Table 13, 'HB 130' has fewer and shorter leaf hairs than Kentucky bluegrasses and most other hybrid bluegrasses.

TABLE 13

Relative hair lengths on leaves from plants allowed to over winter in the field and placed into a controlled greenhouse environment (60-75 F.) in late winter and allowed to grow undisturbed at The Scotts Company facility, Gervais, Oregon. (Rating Scale: 9 = longest hairs, 1 = no hairs).

| Cultivar | Blades-Dorsal | Blades-Upper | Blade-Collar Margin | Sheath-Margin | Ligule-Upper Margin |
|---|---|---|---|---|---|
| 'HB 130' | 0 | 0.9 | 1.3 | 1.3 | 2.1 |
| 'Thermal Blue' | 0 | 0.9 | 3.4 | 4.4 | 4.6 |
| 'Dura Blue' | 0 | 0.8 | 4.3 | 4.1 | 5.8 |
| 'Reveille' | 0 | 0.9 | 2.8 | 4.1 | 5.8 |
| 'Geronimo (Kbg)' | 0 | 1.7 | 1.0 | 1.6 | 2.1 |
| 'Ascot (Kbg)' | 0 | 2.5 | 5.1 | 5.8 | 6.6 |
| 'Tx 51-90 (Tbg)' | 0 | 0.9 | 3.5 | 4.1 | 3.4 |
| 'Tx 39-88 (Tbg)' | 0 | 1.0 | 3.3 | 2.9 | 3.8 |
| 'Tx 49-90 (Tbg)' | 0 | 1.0 | 0.8 | 1.4 | 0.2 |
| lsd (0.05) | 0 | 1.4 | 2.86 | 3.65 | 4.57 |

Since environmental conditions such as soil and climate may influence morphological characteristics to some extent, comparisons of 'HB 130' were made with Kentucky bluegrass varieties under like conditions and the comparisons are set forth in Tables 14–18.

TABLE 14

Heading dates (Julian dates) in years 1 and 2 for field planting of hybrid bluegrasses and parent species.

| Cultivar | Year 1 | Year 2 |
|---|---|---|
| 'HB 130' | 105 | 115 |
| 'Thermal blue' | 108 | 115 |
| 'Dura Blue' | 114 | 105 |
| 'Geronimo' | 105 | 114 |
| 'Ascot' | 110 | 80 |
| 'Tx 19-88' | 120 | 94 |
| 'Tx 46-90' | 113 | 94 |
| 'Tx 4-88' | 103 | 94 |
| lsd (p = 0.05) | 5.55 | 4.3 |

TABLE 15

Anthesis dates in years 1 and 2 for field planting of hybrid bluegrasses and parent species at The Scotts Company facility, Gervais, Oregon.

| Cultivar | Anthesis Date |
|---|---|
| 'HB 130' | 131 |
| 'Thermal Blue' | 131 |
| 'Dura Blue' | 126 |
| 'Geronimo' | 130 |
| 'Ascot' | 127 |
| 'Tx 46-90' | 125 |
| 'Tx 4-88' | 122 |
| lsd (p = 0.05) | 6.0 |

TABLE 16

Heading and anthesis dates for field planting of hybrid bluegrasses and parent species at The Scotts Company facility, Gervais, Oregon.

| Cultivar | Heading Date | Anthesis Date |
|---|---|---|
| 'HB 130' | 122 | 141 |
| 'Thermal Blue' | 120 | 138 |
| 'Dura Blue' | 123 | 145 |
| 'Reveille' | 116 | 141 |
| 'Geronimo' | 122 | 140 |
| 'Ascot' | 124 | 141 |
| 'Tx 51-90' | 116 | 140 |
| 'Tx 39-88' | 121 | — |
| 'Tx 49-90' | 119 | 140 |
| lsd (p = 0.05) | 5.1 | 4.9 |

TABLE 17

Comparison of flowering times of plants allowed to over winter in the field and placed into a controlled greenhouse environment (60-75° F.) in late winter and allowed to grow undisturbed during winter at The Scotts Company facility, Gervais, Oregon.

| Cultivar | Julian date |
|---|---|
| 'HB 130' | 87.1 |
| 'Thermal Blue' | 93.2 |
| 'Dura Blue' | 87.6 |
| 'Reveille' | 89.9 |
| 'Geronimo' | 85.5 |
| 'Ascot' | 87.6 |
| 'Kelly' | 91.8 |
| 'Tx 51-90' | 80.8 |
| 'Tx 39-88' | 84.2 |
| 'Tx 49-90' | 86.7 |
| lsd (p = 0.05) | 5.8 |

TABLE 18

Comparison of growth habit for 'HB 130' to various Kentucky and Texas bluegrass cultivars planted at Gervais, Oregon, after one and two years. (Rating Scale: 1 = prostrate, 2 = semi-erect, and 3 = erect).

| Cultivar | Year 1 | Year 2 |
|---|---|---|
| 'HB-130' | 2.4 | 2.3 |
| 'Thermal Blue' | 2.1 | 2.3 |
| 'Dura Blue' | 1.8 | 2.0 |
| 'Abbey' | 1.0 | 2.4 |
| 'Ascot' | 2.4 | 1.7 |
| 'Geronimo' | 1.9 | 2.3 |
| 'TX 19-88' | 3.0 | 3.0 |
| 'TX 46-90' | 3.0 | 3.0 |
| 'TX 4-88' | 3.0 | 3.0 |
| lsd (p = 0.05) | 0.34 | 0.42 |

The seed of 'HB 130' averages 3.4 mm in length, and 0.83 mm in width.

Comparisons of 'HB 130' with other Kentucky, Texas and hybrid bluegrass varieties in terms of seed length, seed width and 1000 seed weight are shown in Tables 19 and 20 as follows:

TABLE 19

Seed characteristics from panicles of 'HB 130' and comparitor varieties and germplasm.

| Cultivar | Seed Length (mm) | Seed Width (mm) | 1000 Seed Weight (mg) |
|---|---|---|---|
| 'HB 130' | 3.40 | 0.83 | 547 |
| 'Thermal Blue' | 3.20 | 0.80 | 540 |
| 'Dura Blue' | 2.62 | 0.91 | 660 |
| 'Ascot' | 3.23 | 0.80 | 543 |
| 'Geronimo' | 3.03 | 0.81 | 517 |
| 'Tx 46-90' | 3.15 | 0.77 | nd |
| 'Tx 19-88' | 2.20 | 0.69 | nd |
| 'Tx 4-88' | 2.30 | 0.59 | nd |
| lsd (p = 0.05) | 1.09 | 0.80 | 46.8 |

TABLE 20

Thousand seed weight count of hybrid bluegrass grown in eastern Washington

| Cultivar | 1000 Count Seed Weight (mg) |
|---|---|
| 'HB 130' | 417 |
| 'Thermal Blue' | 388 |
| 'Dura Blue' | 513 |
| lsd (p = 0.05) | 11 |

'HB 130' has demonstrated relatively rapid germination and emergence compared to other hybrids including 'HB 129' and 'Reveille' in both fall and spring sowings and a medium turf height 53 days after planting.

TABLE 21

Germination of 'HB 130', hybrid bluegrasses and Kentucky bluegrasses planted in turfgrass plots at Cleveland, Texas observed after 1 or 2 weeks. (Rating Scale: 0 = no germination visible; 9 = all seeds germinated and visible).

| Cultivar | 15 days after seeding | 8 days after seeding |
|---|---|---|
| 'HB 130' | 3.0 | 2.0 |
| 'Thermal Blue' | 2.7 | 1.7 |
| 'Ascot' | 2.7 | 2.7 |
| 'Abbey' | 1.7 | 2.0 |
| 'Coventry' | 1.7 | 1.3 |
| 'Reveille' | 0.0 | 0.0 |
| lsd (0.05) | 0.90 | 0.74 |

TABLE 22

Turf height 53 days after turf planting at The Scotts Company facility at Gervais, Oregon. (Measured in millimeters).

| Cultivar | Turf Height (mm) |
|---|---|
| 'HB 130' | 58.3 |
| 'Thermal Blue' | 80.8 |
| 'Dura Blue' | 41.8 |
| 'Ascot' | 44.6 |
| 'Fairfax' | 85.7 |
| 'Abbey' | 64.1 |
| lsd (0.05) | 19.71 |

'HB 130' has shown greatly reduced seed cotton compared to 'Reveille' and Texas bluegrasses 'Tx 39-88' and 'Tx 49-90'. It is thought that the presence of the cotton on seed has led to poor seed recovery and handling with Texas bluegrasses, and the limits the availability of 'Reveille' predominantly to a vegetative reproduction from rhizome and tiller materials.

TABLE 23

Cotton on lemma. Comparison of Lemma length eyepiece (mm), Lemma length visual %, and cotton length from base (mm) and ranking of visual cotton density for 'HB 130' and various cultivars.

| Cultivar | Lemma length (Eyepiece, in mm) | Cotton length (% of lemma length) | Cotton length (in mm) | Visual cotton density (5 = Most. 1 = None) |
|---|---|---|---|---|
| 'HB 130' | 3.8 | 74.6 | 3.0 | 2.0 |
| 'Thermal Blue' | 3.8 | 80.0 | 3.2 | 2.2 |
| 'Dura Blue' | 4.8 | 108.3 | 4.8 | 3.8 |
| 'Reveille' | 4.2 | 95.4 | 4.0 | 3.0 |
| 'Ascot' | 3.7 | 61.3 | 2.4 | 2.3 |
| 'Geronimo' | 3.8 | 89.6 | 3.3 | 2.3 |
| 'Tx 51-90' | 5.8 | 132.3 | 8.4 | 3.4 |
| 'Tx 39-88' | 6.2 | 133.1 | 7.7 | 3.7 |
| 'Tx 49-90' | 6.2 | 120.8 | 7.7 | 3.7 |
| lsd (p = 0.05) | 0.47 | 26.3 | 1.56 | 0.29 |

TABLE 24

Visual rating of cotton in intact panicles for 'HB 130' and various bluegrass cultivars at Gervais, Oregon. (Rating Scale: 1 = none; 5 = most).

| Cultivar | Intact Panicle Cotton Rating |
|---|---|
| 'HB 130' | 2.3 |
| 'Thermal Blue' | 2.0 |
| 'Dura Blue' | 3.6 |
| 'Geronimo' | 2.1 |
| 'Ascot' | 2.4 |
| 'Tx 39-88' | 3.8 |
| 'Tx 49-90' | 4.3 |
| lsd (p = 0.05) | 0.74 |

'HB 130' has performed well throughout the U.S. as exhibited by good turf quality ratings under standard management inputs in comparison with other Kentucky bluegrass varieties and other Texas×Kentucky bluegrass hybrids. In addition, it has a medium green color with good turf density that can be maintained throughout the growing season providing a rapid development of sod strength, and a medium to high seed yielding capacity.

TABLE 25

Comparison of turf color readings of 'HB 130', various Kentucky bluegrass varieties, and hybrid bluegrass varieties grown in San Diego County, California from winter to winter taken at four different dates during a year. (Rating Scale: 9 = Dark, 1 = Straw Brown).

| Cultivar | March | May | September | January |
|---|---|---|---|---|
| 'HB 130' | 7.0 | 6.0 | 5.7 | 4.3 |
| 'Thermal Blue' | 6.3 | 5.0 | 5.0 | 4.3 |
| 'Dura Blue' | 7.7 | 8.0 | 6.2 | 5.7 |
| 'Abbey' | 6.7 | 5.3 | 5.7 | 5.3 |
| 'Midnight' | 6.7 | 7.0 | 7.8 | 6.0 |
| 'Apollo' | 6.0 | 7.0 | 6.5 | 5.0 |
| lsd (p = 0.05) | 0.67 | 0.98 | 0.76 | 1.2 |

TABLE 26

Winter color ratings at The Scotts Company, Gervais, Oregon. (Rating Scale: 9 = Best; 1 = Worst).

| Cultivar | Winter Color |
|---|---|
| 'HB 130' | 4.3 |
| 'Thermal Blue' | 4.0 |
| 'Dura Blue' | 7.7 |
| 'Avalanche' | 6.3 |
| 'Envicta' | 5.0 |
| lsd (p = 0.05) | 1.1 |

TABLE 27

Leaf characteristics of 'HB 130' and various Kentucky and Texas bluegrass cultivars. In the nursery planted at The Scotts Company facility, Gervais, Oregon. (Measured in centimeters).

| Cultivar | Flag Leaf Blade length | Flag Leaf Sheath length | Vegetative leaf blade length |
|---|---|---|---|
| 'HB 130' | 4.2 | 13.4 | 7.9 |
| 'Thermal Blue' | 4.7 | 12.9 | 7.0 |
| 'DuraBlue' | 4.5 | 11.5 | 7.9 |
| 'Geronimo' | 4.4 | 13.0 | 8.0 |
| 'Ascot' | 3.7 | 9.5 | 6.9 |
| 'Tx 19-88' | 11.3 | 18.5 | 14.2 |

TABLE 27-continued

Leaf characteristics of 'HB 130' and various Kentucky and Texas bluegrass cultivars. In the nursery planted at The Scotts Company facility, Gervais, Oregon. (Measured in centimeters).

| Cultivar | Flag Leaf Blade length | Flag Leaf Sheath length | Vegetative leaf blade length |
|---|---|---|---|
| 'Tx 46-90' | 11.6 | 16.9 | 15.4 |
| lsd (0.05) | 2.79 | 2.15 | 2.68 |

TABLE 28

Comparison flag and vegetative leaf characteristics for 'HB 130' to various Kentucky and Texas bluegrass cultivars in the nursery planted at The Scotts Company facility, Gervais, Oregon. (Measurements in centimeters).

| Cultivar | Flag Blade length | Flag Sheath length | Vegetative leaf blade length |
|---|---|---|---|
| 'HB 130' | 6.5 | 15.3 | 9.0 |
| 'Thermal Blue' | 7.2 | 15.5 | 9.4 |
| 'Dura Blue' | 6.4 | 13.7 | 9.4 |
| 'Reveille' | 7.6 | 16.4 | 9.2 |
| 'Geronimo' | 6.7 | 15.3 | 9.1 |
| 'Ascot' | 5.9 | 13.2 | 9.6 |
| 'Tx 39-88' | 8.7 | 15.8 | 9. |
| 'Tx 49-90' | 9.7 | 15.6 | 12.3 |
| lsd (0.05) | 2.72 | 2.78 | 3.29 |

TABLE 29

Flag leaf length, flag leaf width and vegetative leaf length of plants allowed to over winter in the field and placed into a controlled greenhouse environment (60-75 F.) in late winter and allowed to grow undisturbed at The Scotts Company facility, Gervais, Oregon. (Measured in centimeters).

| Cultivar | Flag Leaf Length | Flag Leaf Width | Vegetative Leaf Length |
|---|---|---|---|
| 'HB 130' | 5.0 | 1.4 | 7.8 |
| 'Thermal Blue' | 4.6 | 1.4 | 8.1 |
| 'Dura Blue' | 4.6 | 1.3 | 8.7 |
| 'Reveille' | 6.7 | 1.3 | 11.7 |
| 'Geronimo' | 4.4 | 1.4 | 7.4 |
| 'Ascot' | 3.9 | 1.2 | 8.0 |
| 'Kelly' | 4.0 | 1.5 | 7.9 |
| 'Tx 51-90' | 8.4 | 1.8 | 9.8 |
| 'Tx 39-88' | 9.2 | 2.0 | 8.7 |
| 'TX 49-90' | 7.3 | 1.7 | 10.6 |
| lsd (p = 0.05) | 1.71 | 0.30 | 2.24 |

'HB 130' resists disease in humid regions better than traditional Kentucky bluegrasses. 'HB 130' is relatively resistance to brown patch and *Pythium* blight. Brown patch, or *Rhizoctonia* blight, is a common summertime disease of cool-season turfgrasses, and is caused by the fungus *Rhizoctonia solani*. Pythium blight, also called cottony blight or grease spot, is a fungal disease of turfgrasses.

'HB 130' shows moderate resistance to rust, dollarspot, and brown blight as demonstrated by the results tabulated in Tables 30 and 31.

TABLE 30

Dollarspot and leaf rust susceptibility of 'HB 130', Kentucky bluegrass varieties, and hybrid bluegrass varieties grown in San Diego County, California. Data is percent of plot area infected.

| Cultivar | Dollarspot | Rust |
|---|---|---|
| 'HB 130' | 16.7 | 13.3 |
| 'Thermal Blue' | 21.7 | 16.7 |
| 'Dura Blue' | 0.3 | 2.0 |
| 'Abbey' | 16.7 | 13.3 |
| 'Midnight' | 0.3 | 26.7 |
| 'Apollo' | 0.0 | 23.3 |
| lsd(p = 0.05) | 10.6 | 10.3 |

TABLE 31

Brown blight susceptibility of 'HB 130', various Kentucky bluegrass varieties, and hybrid bluegrass varieties grown in Gervais, Oregon.

| Cultivar | Percent of Plot Area Infected Brown Blight |
|---|---|
| 'HB 130' | 61.7 |
| 'Thermal Blue' | 66.7 |
| 'Dura Blue' | 5.7 |
| 'Envicta' | 58.3 |
| 'Avalanche' | 25.0 |
| lsd (p = 0.05) | 22.7 |

Color description: The upper and lower leaf blade surface colors of 'HB-130' were determined by comparing several actively growing leaves on at a time, in full sun, with color chips from the Munsell Book of Color as a reference. On this basis, the color of the upper and lower leaf blade surfaces were determined to be nearly comparable; the upper leaf blade surfaces ranged from 5GY 5/6 to 5/8 and the lower leaf blade surfaces ranged from 5GY 4/6 to 5/6. Additionally, color designations were determined from tillers harvested from the plant nursery using the Munsell Book of Color, Volume I of a two volume set, as follows: 10 YR 7/4 to 8/4 for 'HB-130' seed; 10 YR 7/4 to 7/6 for 'HB-130' panicle; and 10 YR 8/4 for 'HB-130' leaf ligule.

What is claimed is:

1. A new and distinct hybrid variety of Texas bluegrass× Kentucky bluegrass plant, as herein illustrated and described and characterized by aggressive rhizome growth, rapid establishment, a medium green, dense turf, a reduced level of cotton on the seed, and a medium to high seed yield potential.

* * * * *